United States Patent [19]

Uekawa et al.

[11] Patent Number: 5,238,906
[45] Date of Patent: Aug. 24, 1993

[54] PYRIDONE DERIVATIVES AND USE

[75] Inventors: Toru Uekawa; Susumu Takemura; Masayuki Enomoto, all of Hyogo; Masaharu Sakai, Osaka, all of Japan; Ryo Sato, Durham, N.C.; Eiki Nagano, Hyogo, Japan

[73] Assignee: Sumitomo Chemical Company, Limited, Osaka, Japan

[21] Appl. No.: 797,069

[22] Filed: Nov. 25, 1991

[30] Foreign Application Priority Data

Nov. 27, 1990 [JP] Japan ................................. 2-326673

[51] Int. Cl.$^5$ ................... C07D 498/02; A01N 43/86
[52] U.S. Cl. .................................... 504/225; 544/105
[58] Field of Search ........................ 544/105; 504/225

[56]  References Cited

U.S. PATENT DOCUMENTS

| 4,729,784 | 3/1988 | Kuhe et al. | 544/105 |
| 4,981,508 | 1/1991 | Strunk et al. | 71/92 |

FOREIGN PATENT DOCUMENTS

| 0216541 | 4/1987 | European Pat. Off. |
| 0255601 | 2/1988 | European Pat. Off. |
| 0259048 | 3/1988 | European Pat. Off. |
| 0311135 | 4/1989 | European Pat. Off. |
| 0328001 | 8/1989 | European Pat. Off. |
| 0338533 | 10/1989 | European Pat. Off. |
| 0408382 | 1/1991 | European Pat. Off. |
| 63-222167 | 3/1987 | Japan. |

9015057 12/1990 World Int. Prop. O.

OTHER PUBLICATIONS

Chemical Abstracts, vol. 111, No. 25, Dec. 18, 1989.

*Primary Examiner*—Nicholas S. Rizzo
*Attorney, Agent, or Firm*—Birch, Stewart, Kolasch & Birch

[57] ABSTRACT

Pyridone derivatives of the formula:

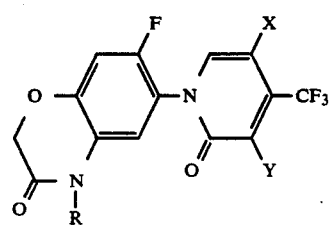

wherein R is an alkyl group, an alkenyl group, an alkynyl group, a haloalkyl group, a haloalkenyl group or an alkoxyalkyl group, X is a hydrogen atom, a halogen atom, a methyl group optionally substituted with mono or poly halogen atoms or an ethyl group optionally substituted with mono or poly halogen atoms and Y is a hydrogen atom or a methyl group. Said compounds show a high herbicidal potency against undesired weeds.

8 Claims, No Drawings

PYRIDONE DERIVATIVES AND USE

BACKGROUND OF THE INVENTION

1. Field of the Invention

The present invention relates to pyridone derivatives, and their production and use. More particularly, it relates to pyridone derivatives, a process for producing them, and their use as herbicides.

2. Description of Related Art

A great number of compounds are known to be effective as the active ingredients in herbicical compositions. Many of them are however are not sufficient in their herbicidal potency or have poor selectivity between crop plants and weeds. Thus, their herbicidal activity is not necessarily adequate. On the other hand, EP-A-0216541 or EP-A-0259048 mentions to an insecticidal utility of certain pyridone compounds but is silent on their utilization as a herbicice.

SUMMARY OF THE INVENTION

As the result of intensive study, it has now been found that pyridone derivatives of the formula:

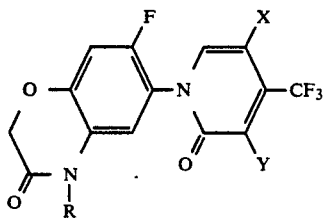

wherein R is an alkyl group, an alkenyl group, an alkynyl group, a haloalkyl group, a haloalkenyl group or an alkoxyalkyl group, X is a hydrogen atom, a halogen atom, a methyl group optionally substituted with mono or poly halogen atoms or an ethyl group optionally substituted with mono or poly halogen atoms and Y is a hydrogen atom or a methyl group show a high herbicidal potency against various weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment. Some of the compounds (I) do not produce any material phytotoxicity on various agricultural crops such as corn, wheat, barley, rice plant, soybean and cotton. Examples of the broadleaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*) hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Pharbitis purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*), spotted spurge (*Euphorbia maculata*), etc.

Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bermudagrass (*Cynodon dactylon*), giant foxtail (*Setaria faberi*), etc.

Examples of Commelinaceous weeds include asiatic dayflower (*Commelina communis*), etc. Examples of the Cyperaceous weeds include rice flatsedge (*Cyperus iria*), etc.

Some of the compounds (I) are also effective in exterminating paddy field weeds including Graminaceous weeds such as barnyardgrass (*Echinochloa oryzoides*), broad-leaved weeds such as common falsepimpernel (*Lindernia procumbens*), indian toothcup (*Rotala indica*) and waterwort (*Elatine triandra*), Cyperaceous weeds such as hardstem bulrush (*Scirpus juncoides*), needle spikerush (*Eleocharis acicularis*) and umbrella sedge (*Cyperus difformis*), and others such as monochoria (*Monochoria vaginalis*) and arrowhead (*Sagittaria pygmaea*) without producing any phytotoxicity to rice plants on flooding treatment.

In the above significances, the substituent R represents a $C_1$-$C_8$ alkyl group (e.g. methyl, ethyl, n-propyl, isopropyl, n-butyl, isobutyl, sec-butyl, n-pentyl, n-hexyl, n-heptyl, n-octyl), a $C_3$-$C_7$ alkenyl group (e.g. 2-propenyl, 1-methyl-2-propenyl, 2-butenyl, 1-methyl-2-butenyl, 3-methyl-2-butenyl, 1,3-dimethyl-2-butenyl, 2-methyl-2-propenyl, 1,2-dimethyl-2-propenyl, 1,2,3-trimethyl-2-butenyl, 2,3-dimethyl-2-butenyl, 2-methyl-2-butenyl, 1,2-dimethyl-2-butenyl), a $C_3$-$C_6$ alkynyl group (e.g. 2-propynyl, 1-methyl-2-propynyl, 2-butynyl, 1-methyl-2-butynyl, 2-pentynyl, 1-methyl-2-pentynyl, 3-butynyl, 1-methyl-3-butynyl, 1,2-dimethyl-3-butynyl), a $C_1$-$C_4$ alkoxy($C_1$-$C_2$)alkyl group (e.g. methoxymethyl, 1-methoxyethyl, ethoxymethyl, 1-ethoxyethyl, n-propoxymethyl, isopropoxymethyl, 1-(n-propoxy)ethyl, n-butoxymethyl, 1-(n-butoxy)ethyl, methoxyethyl, ethoxyethyl, 1-methyl-2-methoxyethyl, 1-methyl-2-ethoxyethyl, n-propoxyethyl, n-butoxyethyl, 1-methyl-2-(n-butoxy)ethyl), a $C_2$-$C_4$ haloalkyl group (e.g. 2-fluoroethyl, 2,2-difluoroethyl, 2,2,2-trifluoroethyl, 2-chloroethyl), a $C_3$-$C_4$ haloalkenyl group (e.g. 3-chloro-2-propenyl, 2-chloro-2-propenyl, 2,3-dichloro-2-propenyl, 2-chloro-1-methyl-2-propenyl), etc. The substituent represented by X includes hydrogen, fluorine, chlorine, bromine, methyl, ethyl, fluoromethyl, difluoromethyl or fluoroethyl, etc.

Among the compounds (I), preferred are those wherein R is a $C_2$-$C_4$ alkyl group, a $C_3$-$C_4$ alkenyl group, a $C_3$-$C_4$ alkynyl group, a 2-fluoroethyl group or a $C_1$-$C_3$ alkoxymethyl group, X is a hydrogen atom, a fluorine atom, a chlorine atom, a bromine atom, a methyl group, a fluoromethyl group or a difluoromethyl group and Y is a hydrogen atom or a methyl group. More preferred are those wherein R is an n-propyl group, an isopropyl group, a sec-butyl group, a $C_3$-$C_4$ alkenyl group, a $C_3$-$C_4$ alkynyl group, a 2-fluoroethyl group or a methoxymethyl group, X is a fluorine atom, a chlorine atom, a bromine atom or a methyl group and Y is a hydrogen atom or a methyl group. Typical examples of the preferred compounds are 1-(7-fluoro-4-propargyl-3-oxo-3,4-dihydro-2H-1,4-benzoxazin-6-yl)-4-trifluoromethyl -2-pyridone, 5-chloro-1-(7-fluoro-4-propargyl-3-oxo-3,4-dihydro-2H-1,4-benzoxazin-6-yl) -4-trifluoromethyl-2-pyridone, 1-(7-fluoro-4-propargyl-3-oxo-3,4-dihydro-2H-1,.4-benzoxazin-6-yl) -5-methyl-4-trifluoromethyl-2-pyridone, etc.

Production of the compounds (I) according to the invention is explained below.

The compound (I) can be synthetized by reacting a compound of the formula:

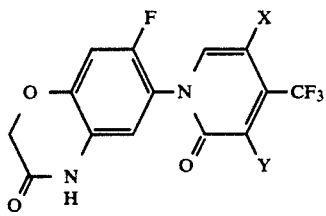

wherein X and Y are each as defined above with a compound of the formula:

R-W    (III)

wherein W is a chlorine atom, a bromine atom, an iodine atom, a p-toluenesulfonyloxy group or a methanesulfonyloxy group and R is as defined above.

The reaction is usually carried out in a solvent at a temperature of about 0° to 100° C. for a period of about 0.5 to 10 hours in the presence of a base.

The compound (III) and the base are each used in an amount of about 1 to 2 equivalents to one equivalent of the compound (II).

Examples of the solvent are aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), alcohols (e.g. methanol, ethanol, isopropanol, t-butanol, octanol, cyclohexanol, methylcello-solve, diethylene glycol, glycerin), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulforan), liquid ammonia, water, etc. These may be used solely or in combination.

As the base, there may be used an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

After completion of the reaction, the reaction mixture is subjected to ordinary post-treatment. For instance, the reaction mixture is poured into water, and the precipitated crystals are collected by filtration or extracted with an organic solvent, followed by concentration. If desired, any conventional purification procedure such as chromatography, distillation or recrystallization may be applied to the resulting product to obtain the objective compound.

In the same manner as above, the compounds (I) as shown in Table 1 are obtainable.

TABLE 1

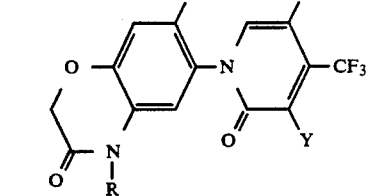

| R | Y | Y |
|---|---|---|
| $CH_3$ | H | H |
| $C_2H_5$ | H | H |
| $n$-$C_3H_7$ | H | H |
| iso-$C_3H_7$ | H | H |
| $n$-$C_4H_9$ | H | H |
| iso-$C_4H_9$ | H | H |
| sec-$C_4H_9$ | H | H |
| $n$-$C_5H_{11}$ | H | H |
| $n$-$C_6H_{13}$ | H | H |
| $CH_2CH=CH_2$ | H | H |
| $CH_2CH=CHCH_3$ | H | H |
| $CHCH=CH_2$<br>\|<br>$CH_3$ | H | H |
| $CHCH=CHCH_3$<br>\|<br>$CH_3$ | H | H |
| $CH_2C=CH_2$<br>\|<br>$CH_3$ | H | H |
| $CH_2C=CHCH_3$<br>\|<br>$CH_3$ | H | H |
| $CH_2C\equiv CH$ | H | H |
| $CHC\equiv CH$<br>\|<br>$CH_3$ | H | H |
| $CH_2OCH_3$ | H | H |
| $CHOCH_3$<br>\|<br>$CH_3$ | H | H |
| $CH_2CH_2OCH_3$ | H | H |
| $CH_2CH_2OCH_2CH_3$ | H | H |
| $CH_2CH_2F$ | H | H |
| $CH_2CH_2Cl$ | H | H |
| $CH_2CF_3$ | H | H |
| $CH_2CCl=CH_2$ | H | H |
| $CHCCl=CH_2$<br>\|<br>$CH_3$ | H | H |
| $CH_2CH=CH$<br>\|<br>$Cl$ | H | H |
| $CH_3$ | Cl | H |
| $C_2H_5$ | Cl | H |
| $n$-$C_3H_7$ | Cl | H |
| iso-$C_3H_7$ | Cl | H |
| $n$-$C_4H_9$ | Cl | H |
| iso-$C_4H_9$ | Cl | H |
| sec-$C_4H_9$ | Cl | H |
| $n$-$C_5H_{11}$ | Cl | H |
| $n$-$C_6H_{13}$ | Cl | H |
| $CH_2CH=CH_2$ | Cl | H |

TABLE 1-continued (I)

| R | Y | Y |
|---|---|---|
| CH₂CH=CHCH₃ | Cl | H |
| CHCH=CH₂ (CH₃) | Cl | H |
| CHCH=CHCH₃ (CH₃) | Cl | H |
| CH₂C=CH₂ (CH₃) | Cl | H |
| CH₂C=CHCH₃ (CH₃) | Cl | H |
| CH₂C≡CH | Cl | H |
| CHC≡CH (CH₃) | Cl | H |
| CH₂OCH₃ | Cl | H |
| CHOCH₃ (CH₃) | Cl | H |
| CH₂CH₂OCH₃ | Cl | H |
| CH₂CH₂OCH₂CH₃ | Cl | H |
| CH₂CH₂F | Cl | H |
| CH₂CH₂Cl | Cl | H |
| CH₂CF₃ | Cl | H |
| CH₂CCl=CH₂ | Cl | H |
| CHCCl=CH₂ (CH₃) | Cl | H |
| CH₂CH=CH (Cl) | Cl | H |
| CH₃ | Br | H |
| C₂H₅ | Br | H |
| n-C₃H₇ | Br | H |
| iso-C₃H₇ | Br | H |
| n-C₄H₉ | Br | H |
| iso-C₄H₉ | Br | H |
| sec-C₄H₉ | Br | H |
| n-C₅H₁₁ | Br | H |
| n-C₆H₁₃ | Br | H |
| CH₂CH=CH₂ | Br | H |
| CH₂CH=CHCH₃ | Br | H |
| CHCH=CH₂ (CH₃) | Br | H |
| CHCH=CHCH₃ (CH₃) | Br | H |
| CH₂C=CH₂ (CH₃) | Br | H |
| CH₂C=CHCH₃ (CH₃) | Br | H |
| CH₂C≡CH | Br | H |
| CHC≡CH (CH₃) | Br | H |
| CH₂OCH₃ | Br | H |
| CHOCH₃ (CH₃) | Br | H |
| CH₂CH₂OCH₃ | Br | H |
| CH₂CH₂OCH₂CH₃ | Br | H |
| CH₂CH₂F | Br | H |
| CH₂CH₂Cl | Br | H |
| CH₂CF₃ | Br | H |
| CH₂CCl=CH₂ | Br | H |
| CHCCl=CH₂ (CH₃) | Br | H |
| CH₂CH=CH (Cl) | Br | H |
| CH₃ | CH₃ | H |
| C₂H₅ | CH₃ | H |
| n-C₃H₇ | CH₃ | H |
| iso-C₃H₇ | CH₃ | H |
| n-C₄H₉ | CH₃ | H |
| iso-C₄H₉ | CH₃ | H |
| sec-C₄H₉ | CH₃ | H |
| n-C₅H₁₁ | CH₃ | H |
| n-C₆H₁₃ | CH₃ | H |
| CH₂CH=CH₂ | CH₃ | H |
| CH₂CH=CHCH₃ | CH₃ | H |
| CHCH=CH₂ (CH₃) | CH₃ | H |
| CHCH=CHCH₃ (CH₃) | CH₃ | H |
| CH₂C=CH₂ (CH₃) | CH₃ | H |
| CH₂C=CHCH₃ (CH₃) | CH₃ | H |
| CH₂C≡CH | CH₃ | H |

TABLE 1-continued

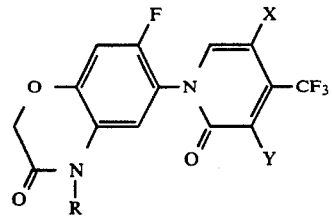

| R | X | Y |
|---|---|---|
| CHC≡CH(CH3) | CH3 | H |
| CH2OCH3 | CH3 | H |
| CHOCH3(CH3) | CH3 | H |
| CH2CH2OCH3 | CH3 | H |
| CH2CH2OCH2CH3 | CH3 | H |
| CH2CH2F | CH3 | H |
| CH2CH2Cl | CH3 | H |
| CH2CF3 | CH3 | H |
| CH2CCl=CH2 | CH3 | H |
| CHCCl=CH2(CH3) | CH3 | H |
| CH2CH=CH(Cl) | CH3 | H |
| C2H5 | C2H5 | H |
| n-C3H7 | C2H5 | H |
| iso-C3H7 | C2H5 | H |
| n-C4H9 | C2H5 | H |
| iso-C4H9 | C2H5 | H |
| sec-C4H9 | C2H5 | H |
| CH2CH=CH2 | C2H5 | H |
| CH2CH=CHCH3 | C2H5 | H |
| CHCH=CH2(CH3) | C2H5 | H |
| CH2C=CH2(CH3) | C2H5 | H |
| CH2C≡CH | C2H5 | H |
| CHC≡CH(CH3) | C2H5 | H |
| CH2OCH3 | C2H5 | H |
| CHOCH3(CH3) | C2H5 | H |
| CH2CH2OCH3 | C2H5 | H |
| CH2CH2OCH2CH3 | C2H5 | H |
| CH2CH2F | C2H5 | H |
| CH2CH2Cl | C2H5 | H |
| CH2CF3 | C2H5 | H |
| CH2CCl=CH2 | C2H5 | H |
| CHCCl=CH2(CH3) | C2H5 | H |
| CH3 | H | CH3 |
| C2H5 | H | CH3 |

TABLE 1-continued

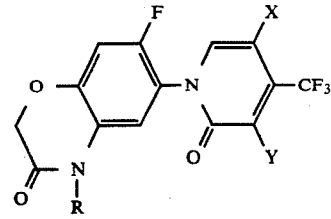

| R | X | Y |
|---|---|---|
| n-C3H7 | H | CH3 |
| iso-C3H7 | H | CH3 |
| n-C4H9 | H | CH3 |
| iso-C4H9 | H | CH3 |
| sec-C4H9 | H | CH3 |
| n-C5H11 | H | CH3 |
| n-C6H13 | H | CH3 |
| CH2CH=CH2 | H | CH3 |
| CH2CH=CHCH3 | H | CH3 |
| CHCH=CH2(CH3) | H | CH3 |
| CHCH=CHCH3(CH3) | H | CH3 |
| CH2C=CH2(CH3) | H | CH3 |
| CH2C=CHCH3(CH3) | H | CH3 |
| CH2C≡CH | H | CH3 |
| CHC≡CH(CH3) | H | CH3 |
| CH2OCH3 | H | CH3 |
| CHOCH3(CH3) | H | CH3 |
| CH2CH2OCH3 | H | CH3 |
| CH2CH2OCH2CH3 | H | CH3 |
| CH2CH2F | H | CH3 |
| CH2CH2Cl | H | CH3 |
| CH2CF3 | H | CH3 |
| CH2CCl=CH2 | H | CH3 |
| CHCCl=CH2(CH3) | H | CH3 |
| CH2CH=CH(Cl) | H | CH3 |

Still, some of the compounds of the invention have an asymmetric carbon atom and accordingly any optical isomer due to such carbon atom is also included within the scope of the compounds (I) of the invention.

A practical embodiment for production of the compound (I) is shown in the following Production Example.

EXAMPLE 1

Production of Compound No. 3

To a solution of 1-(7-fluoro-3-oxo-3,4-dihydro-2H-1,4-benzoxadin-6-yl) -4-trifluoromethyl-2-pyridone (492 mg) in dimethylformamide (2.0 ml), propargyl bromide (357 mg) and potassium carbonate (414 mg) were added, and the resultant mixture was heated at 20° to 40° C. for 2 hours. Upon termination of the reaction, the reaction mixture was poured into water and extracted with ethyl acetate, and the extract was washed with water, dried over anhydrous magnesium sulfate and concentrated in vacuo. The residue was washed with diethyl ether to give the objective compound (444 mg) as colorless crystals.

$^1$H-NMR (CDCl$_3$, 60 MHz) δ (ppm): 2.45 (q, J=2 Hz, 1H), 4.65 (d, J=2 Hz, 2H), 4.70 (s, 2H), 6.45 (d, J=6 Hz, 1H), 6.78 (bs, 1H), 7.05 (d, J=11 Hz, 1H), 7.32 (d, J=7 Hz, 1H), 7.72 (d, J=7 Hz, 1H).

In the same manner as above, the compounds as shown in Table 2 were obtained.

TABLE 2

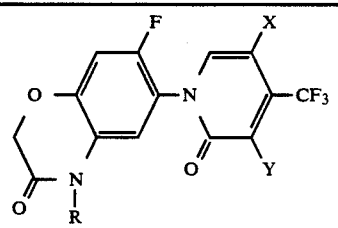

(I)

| Compound No. | X | Y | R | Physical property |
|---|---|---|---|---|
| 1 | H | H | C$_2$H$_5$ | m.p., 264.0° C. |
| 2 | H | H | CH$_2$CH=CH$_2$ | m.p., 205.0° C. |
| 3 | H | H | CH$_2$C≡CH | m.p., 229.6° C. |
| 4 | H | H | CH$_2$CH$_2$F | m.p., 251.5° C. |
| 5 | H | H | CH$_2$CCl=CH$_2$ | m.p., 107.4° C. |
| 6 | H | H | CH$_2$OCH$_3$ | m.p., 227.2° C. |
| 7 | H | H | CH$_2$OC$_2$H$_5$ | m.p., 191.1° C. |
| 8 | CH$_3$ | H | CH$_2$C≡CH | m.p., 141–143° C. |
| 9 | Cl | H | CH$_2$C≡CH | m.p., 215.5–218° C. |
| 10 | Br | H | CH$_2$C≡CH | m.p., 210–211° C. (decomp.) |
| 11 | C$_2$H$_5$ | H | CH$_2$C≡CH | m.p., 224–226° C. |

The starting compound (II) as well as the intermediary compounds are synthesized according to the following reaction scheme:

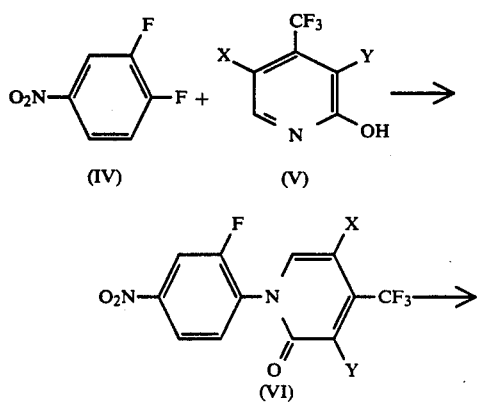

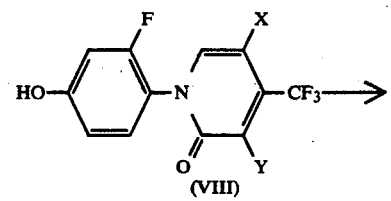

(VII)

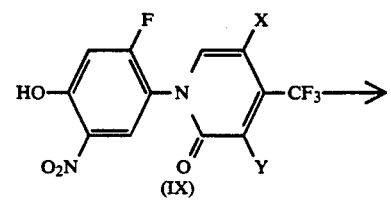

(VIII)

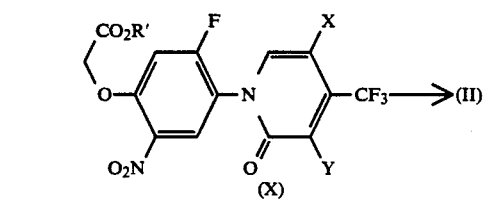

(IX)

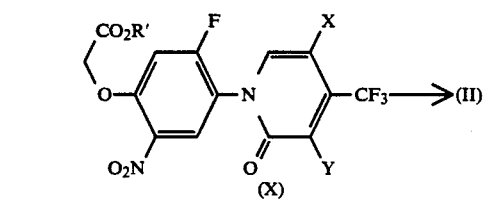

(X) →(II)

wherein R' is an alkyl group and X and Y are each as defined above.

The above reaction is specifically explained below.

Step (A)

Production of the Compound (VI) From the Compound (IV)

The compound (IV) is reacted with the compound (V) in the presence or absence of a solvent in the existence of a base at a temperature of 0° to 100° C. for a period of 0.5 to 24 hours. The compound (V) and the base are used respectively in amounts of 1 to 1.1 equivalents and 1 to 2 equivalents to one equivalent of the compound (IV).

As the solvent, there may be exemplified aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), alcohols (e.g. methanol, ethanol, isopropanol, t-butanol, octanol, cyclohexanol, 2-methoxyethanol, diethylene glycol, glycerin), esters (e.g. ethyl formate, ethyl acetate, butyl acetate, diethyl carbonate), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulforan), liquid ammonia, water, etc. These may be used solely or in combination.

Examples of the base are an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

After completion of the reaction, the reaction mixture is subjected to ordinary post-treatment. For instance, the reaction mixture is poured into water, and the precipitated crystals are collected by filtration or extracted with an organic solvent, followed by concentration. If desired, any conventional purification procedure such as chromatography and recrystallization may be applied to give the objective compound (VI).

The compound (V) may be prepared by the method as disclosed in EP-A-0259048.

A practical embodiment for production of the compound (VI) is shown in the following example.

Production Example 2 (Compound (VI))

To a suspension of sodium hydride (9.2 g) in N,N-dimethylformamide (100 ml), a solution of 2-hydroxy-4-trifluoromethylpyridine (Compounv (V)) (53 g) in N,N-dimethylformamide (100 ml) was added under ice-cooling, and the resultant mixture was heated to room temperature. 3,4-Difluoronitrobenzene (Compound (IV)) (51 g) was dropwise added. thereto, and the mixture was stirred at 80° to 90° C. for 11 hours. Upon termination of the reaction, the reaction mixture was poured into water and extracted with ethyl acetate. The extract was washed with water, dried over anhydrous magnesium sulfate and concentrated. The residue was washed with diethyl ether to give the objective compound (45 g) as yellow crystals.

In the same manner as above, the compounds (VI) as shown in Table 3 were obtained.

TABLE 3

$$O_2N-\underset{}{\bigcirc}\underset{F}{-}N\underset{O}{\overset{X}{\bigcirc}}\underset{Y}{-}CF_3 \quad (VI)$$

| X | Y | Physical property |
| --- | --- | --- |
| H | H | m.p., 130.5° C. |
| CH₃ | H | m.p., 99-101° C. |
| H | CH₃ | m.p., 109-111° C. |
| Cl | H | orange oil; ¹H-NMR(CDCl₃, 60MHz)δ(ppm): 6.92(bs, 1H), 7.48(bs, 1H), 7.58(dd, 1H, J=6Hz, 8Hz), 7.90-8.20(m, 2H) |
| Br | H | m.p., 192-194° C. |
| C₂H₅ | H | m.p., 115.5-116° C. |

Step (B)

Production of the Compound (VII) From the Compound

The compound (VII) is obtainable by reducing the compound (VI) in a solvent in the presence of a reducing agent, of which specific example are an agent comprising a metal (e.g. iron, tin) and a protonic acid, or a metal (e.g. platinum, palladium) and hydrogen, etc. The same solvent(s) as used in Step (A) and fatty acids (e.g. formic acid, acetic acid, oleinic acid) are applicable in this reaction.

After completion of the reaction, the reaction mixture is subjected to ordinary post-treatment. For instance, after removal of insoluble materials, the reaction mixture is extracted with an organic solvent, followed by concentration. If desired, any conventional purification procedure such as chromatography and recrystallization may be applied to give the objective compound (VII).

A practical embodiment for production of the compound (VII) is shown in the following example.

Production Example 3 (Compound (VII)

A mixture of iron powders (40 g), acetic acid (450 ml) and water (50 ml) was vigorously stirred at 80° C., and a solution of 1-(2-fluoro-4-nitrophenyl)-4-trifluoromethyl-2-pyridone (Compound (VI)) (43 g) in ethyl acetate (100 ml) was dropwise added thereto, followed by heating under reflux for 2 hours. Upon termination of the reaction, the reaction mixture was filtered on celite, and the filtrate was poured into water and extracted with ethyl acetate. The extract was washed with a saturated sodium hydrogen carbonate solution, dried over anhydrous magnesium sulfate and concentrated to give the objective compound (38 g) as yellow crystals.

In the same manner as above, the compounds (VII) as shown in Table 4 were obtained.

TABLE 4

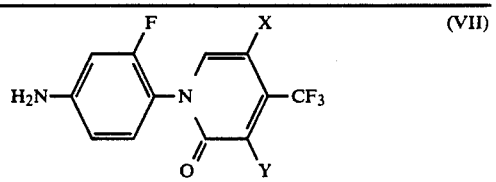

| X | Y | Physical property |
| --- | --- | --- |
| H | H | m.p., 168.9° C. |
| CH₃ | H | m.p., 193.5-194° C. |
| H | CH₃ | m.p., 124.5-126° C. |
| Cl | H | m.p., 167° C. |
| Br | H | m.p., 192-194° C. |
| C₂H₅ | H | m.p., 203-204° C. (decomp.) |

Step (C)

Production of the Compound (VIII) From the Compound (VII)

The compound (VII) is treated with sodium nitrite to give a diazonium salt which is, without isolation, further subjected to decomposition of the diazonium salt.

The diazotization is normally performed in the presence of an acid (e.g. sulfuric acid) at a temperature of about −10° to 10° C. for a period of 1 to 5 hours. Sodium nitrite is used in an amount of 1 to 2 equivalents to one equivalent of the compound (VII). The subsequent decomposition is in general carried out in a solvent (e.g. water) in the presence or absence of an acid (e.g. sulfuric acid) at a temperature of 80° to 120° C. for a period of about 0.5 to 2 hours.

After completion of the reaction, the reaction mixture is subjected to ordinary post-treatment such as extraction with an organic solvent and concentration, etc. If necessary, any purification procedure such as chromatography and recrystallization may be adopted to give the objective compound (VIII).

A practical embodiment for production of the compound (VIII) is shown in the following example.

Production Example 4 (Compound VIII))

A mixture of 1-(4-amino-2-fluorophenyl)-4-trifluoromethyl-2-pyridone (Compound (VII)) (21 g), 98% sulfuric acid (24 g) and water (200 ml) was stirred at 80° C. for 1 hour, followed by ice-cooling. A solution of sodium nitrite (5.9 g) in water (60 ml) was dropwise added thereto at 5° to 10° C., and the resultant mixture was stirred at the same temperature for 1 hour. The reaction mixture was filtered on celite and the filtrate was dropwise added to a saturated sodium sulfate solution (300 ml) at 100° C., followed by stirring at 100° C. for 10 minutes. Upon termination of the reaction, the reaction mixture was extracted with ether, dried over anhydrous magnesium sulfate and concentrated. The residue was washed with chloroform to give the objective compound (8 g) as yellow crystals.

In the same manner as above, the compounds (VIII) as shown in Table 5 were obtained.

TABLE 5

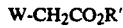

(VIII)

| X | Y | Physical property |
|---|---|---|
| H | H | m.p., 209–211° C. |
| $CH_3$ | H | m.p., 230–231° C. |
| H | $CH_3$ | m.p., 173–174° C. |
| Cl | H | m.p., 248–249° C. |
| Br | H | m.p., 270–271° C. |
| $C_2H_5$ | H | m.p., 211–212° C. (decomp.) |

Step (D)

Production of the Compound (IX) From the Compound (VIII)

The compound (IX) is obtainable by nitratio the compound (VIII) with nitric acid. The reaction is normally performed in the absence or presence of a solvent at a temperature of about −20° to 20° C. for a period of 0.5 to hours. Nitric acid is used in an amount of 1 to 1.1 equivalents to one equivalent of the compound (VIII).

As the solvent, there may be used halogenated hydrocarbons (e.g. chloroform, carbon tetrachloride, dichloroethane), water, or their mixture(s).

After completion of the reaction, the reaction mixture is subjected to ordinary post-treatment such as extraction with an organic solvent and concentration, etc. If necessary, any purification procedure such as chromatography and recrystallization may be adopted to give the objective compound (IX).

A practical embodiment for production of the compound (IX) is shown in the following example.

Production Example 5 (Compound (IX))

To fuming nitric acid (25 ml), 1-(2-fluoro-4-hydroxyphenyl)-4-trifluoromethyl-2-pyridone (Compound (VIII)) (6.9 g) was slowly added at −5° to 0° C., followed by gradual heating to room temperature. Upon termination of the reaction, the reaction mixture was poured into water, extracted with ethyl acetate, and the extract was dried over anhydrous magnesium sulfate and concentrated. The residue was purified by silica gel column chromatography to give the objective compound (6.5 g) as yellow crystals.

In the same manner as above, the compounds (IX) as shown in Table 6 were obtained.

TABLE 6

(IX)

| X | Y | Physical property |
|---|---|---|
| H | H | m.p., 177.8° C. |
| $CH_3$ | H | m.p., 146° C. (decomp.) |
| Cl | H | m.p., 117–118° C. |
| Br | H | $^1$H-NMR(CDCl$_3$, 60MHz)δ(ppm): 6.94(d, 1H, J=10Hz), 6.93(bs, 1H), 7.45(bs, 1H), 8.11(d, 1H, J=7Hz) |

Step (E)

Production of the Compuond (X) From the Compound (IX)

The compound (X) is produced by reacting the compound (IX) with a compound of the formula:

$$W\text{-}CH_2CO_2R' \qquad (XI)$$

wherein W and R' are each as defined above.

This reaction is normally carried out in a solvent in the presence of a base at a temperature of 0° to 100° C. for a period of 0.5 to 10 hours. The compound (XI) and the base are respectively used in 1 to 2 equivalents to one equivalent of the compound (IX).

As the solvent, there may be exemplified aliphatic hydrocarbons (e.g. hexane, heptane, ligroin, petroleum ether), aromatic hydrocarbons (e.g. benzene, toluene, xylene), halogenated hydrocarbons (e.g. chloroform, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), alcohols (e.g. methanol, ethanol, isopropanol, t-butanol, octanol, cyclohexanol, 2-methoxyethanol, diethylene glycol, glycerin), esters (e.g. ethyl formate, ethyl acetate, butyl acetate, diethyl carbonate), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulforan), liquid ammonia, water, etc. These may be used solely or in combination.

Examples of the base are an organic base (e.g. pyridine, triethylamine, N,N-diethylaniline), an inorganic base e.g. sodium hydroxide, potassium hydroxide, sodium carbonate, potassium carbonate, sodium hydride), an alkali metal alkoxide (e.g. sodium methoxide, sodium ethoxide), etc.

After completion of the reaction, the reaction mixture is subjected to ordinary post-treatment. For instance, the reaction mixture is poured into water, and the precipitated crystals are collected by filtration or extracted with an organic solvent, followed by concentration. If desired, any conventional purification procedure such as chromatography and recrystallization may be applied to give the objective compound (X).

A practical embodiment for production of the compound (X) is shown in the following example.

Production Example 6 (Compound (X))

To a suspension of sodium hydride (0.64 g) in N,N-dimethylformamide (10 ml), a solution of 1-(2-fluoro-4-hydroxy-5-nitrophenyl)-4-trifluoromethyl-2-pyridone (Compound (IX)) (4.9 g) in N,N-dimethylformamide (20 ml) was added, and the resultant mixture was stirred at room temperature for 30 minutes. Methyl bromoacetate (Compound (XI)) (4 g) was dropwise added thereto, and the mixture was heated at 50° C. for 3 hours. Upon termination of the reaction, the reaction mixture was poured into water and extracted with ethyl acetate. The extract was washed with water, dried over anhydrous magnesium sulfate and concentrated. The residue was washed with ether to give the objective compound (4.9 g) as yellow crystals.

In the same manner as above, the compounds (X) as shown in Table 7 were obtained.

TABLE 7

[Structure: CO₂R'-O- phenyl with F, O₂N substituents -N- pyridone ring with X, Y, CF₃, O]

| X | Y | R' | Physical property |
|---|---|---|---|
| H | H | $CH_3$ | m.p., 164.6° C. |
| Cl | H | $C_2H_5$ | m.p., 219.6° C. |
| Br | H | $CH_3$ | m.p., 221–222° C. |
| $CH_3$ | H | $C_2H_5$ | $^1$H-NMR(CDCl$_3$, 60MHz)δ(ppm): 1.30(t, J=7Hz, 3H), 2.17(bs, 3H), 4.30(q, J=7Hz, 2H), 4.82(bs, 2H), 6.80(d, J=10Hz, 1H), 6.90(bs, 1H), 7.22(bs, 1H), 7.98(d, J=6Hz, 1H) |

Step (F)

Production of the Compound (II) from the Compound (X)

The compound (II) is obtainable by reducing the compound (X). The reaction is normally performed in a solvent in the presence of a reducing agent at a temperature of 70° to 150° C. for a period of 10 minutes to 2 hours.

As the reducing agent, there may be used an agent comprising a metal (e.g. iron, tin) and protonic acid or an agent comprising a metal (e.g. platinum, palladium) and hydrogen, etc.

Examples of the solvent are aliphatic hydrocarbons (e.g. hexane, heptane, ligroin), aromatic hydrocarbons (e.g. benzene, toluene, xylene), halogenated hydrocarbons (e.g. chloroform, dichloroethane, carbon tetrachloride, chlorobenzene, dichlorobenzene), ethers (e.g. diisopropyl ether, dioxane, tetrahydrofuran, ethylene glycol dimethyl ether), ketones (e.g. methyl isobutyl ketone, isophorone, cyclohexanone), fatty acids (e.g. formic acid, acetic acid, oleinic acid), alcohols (e.g. ethanol, isopropanol, t-butanol, octanol, cyclohexanol, 2-methoxyethanol, diethylene glycol, glycerin), esters (e.g. ethyl formate, ethyl acetate, butyl acetate, diethyl carbonate), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulforan), water, etc. These may be used solely or in combination.

After completion of the reaction, the reaction mixture is subjected to conventional post-treatment. For instance, insoluble materials are removed by filtration, and the filtrate is extracted with an organic solvent and concentrated. If necessary, any purification procedure such as chromatography and recrystallization may be adopted to give the objective compound (II).

A practical embodiment for production of the compound (II) is shown in the following example.

Production Example 7 (Compound (II))

A solution of 1-(2-fluoro-4-methoxycarbonylmethoxy-5-nitrophenyl)-4-trifluoromethyl-2-pyridone (Compound (X)) (4.5 g) in ethyl acetate (60 ml) and acetic acid (20 ml) was dropwise added to a mixture of iron powders (4 g), acetic acid (40 ml) and water (10 ml) while vigorously stirring at 80° C. Upon termination of the reaction, the reaction mixture was filtered on celite and the filtrate was poured into water and extracted with ethyl acetate. The extract was washed with water and a saturated sodium hydrogen carbonate, dried over anhydrous magnesium sulfate and concentrated. The residue was washed with ether to give the objective compound (3.1 g) as colorless crystals.

In the same manner as above, the compounds (II) as shown in Table 8 were obtained.

TABLE 8

[Structure: O-CH₂-C(=O)-NH- attached to phenyl with F, connected to N-pyridone ring with X, Y, CF₃, O]

| X | Y | Physical property |
|---|---|---|
| H | H | m.p., 283–285° C. |
| Cl | H | m.p., >300° C. |
| Br | H | m.p., >300° C. |
| $CH_3$ | H | viscous oil |

For the practical usage of the compound (I), it is usually formulated with conventional solid or liquid carriers or diluents as well as surface active agents or auxiliary agents into conventional preparation forms such as emulsifiable concentrates, wettable powders, flowables, granules and water-dispersible granules. The content of the compound (I) as the active ingredient in such preparation forms is normally within a range of about 0.03 to 80% by weight, preferably of about 0.05 to 70% by weight.

Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

The compound (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the compound (I) over the top of plants. It may also be applied directly to the weeds if care is taken to keep the chemical off the crop foliage.

The compound (I) may be used together with any other herbicide to improve its activity as a herbicide. Further, it may be applied in combination with an insecticide, an acaricide, a nematocide, a fungicide, a plant growth regulator, a fertilizer, a soil improver, etc. Still, the compound (I) as the herbicide is not only applicable to paddy fileds and plowed fields but also to orchards, pasture lands, lawns, forests and non-agricultural fields, etc.

The compound (I) may be also used as an active ingredient of a harvestaid agent such as cotton defoliant, cotton desiccant and potato desiccant, etc. to facilitate harvesting.

The dosage of the compound (I) may vary depending on the prevailing weather conditions, the formulation used, the prevailing season, the modes of application, the soil involved, the crop and weed species, etc. Generally, however, the dosage is from about 0.05 to 80 grams, preferably from about 0.15 to 40 grams, of the active ingredient per are. The herbicidal composition of the invention formulated in the form of an emulsifiable concentrate, a wettable powder or flowables may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietic acid salt, dinaphthylmethanedisulfonate, paraffin, etc. The composition formulated in the form of granules may be normally applied as such without any dilution.

Practical embodiments of the herbicidal composition according to the present invention are illustratively shown in the following examples wherein parts are by weight. The number of the active ingredient corresponds to the one in Table 2.

Formulation Example 1

Fifty parts of any one of Compound 7 Nos. 1 to 11, 3 parts of calcium ligninsulfonate, 2 parts of sodium laurylsulfate and 45 parts of synthetic hydrous silicate are well mixed while being powdered to obtain a wettable powder.

Formulation Example 2

Five parts of any one of Compound Nos. 1 to 11, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

Formulation Example 3

Two parts of any one of Compound 7 Nos 1 to 11, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

Formulation Example 4

Twenty-five parts of any one of Compound Nos. 1 to 11 are mixed with 3 parts of polyoxyethylene sorbitan monooleate, 3 parts of CMC (carboxymethyl cellulose) and 69 parts of water, and the resultant mixture is pulverized until the particle size of the mixture becomes less than 5 microns to obtain a flowable.

The biological data of the compound (I) as herbicides will be illustratively shown in the following Test Examples wherein the phytotoxicity to crop plants and the herbicidal activity on weeds were observed visually as to the degree of germination as well as the growth inhibition and rated with an index 0, 1, 2, 3, 4 or 5, the number "0" indicating no material difference as seen in comparison with the untreated plants and the number "5" indicating the complete inhibition or death of the test plants.

The compounds as shown in Table 9 were used for comparison.

TABLE 9

| Compound No. | Structure | Remarks |
|---|---|---|
| A | Cl, Cl, Cl substituted diphenyl ether with NO$_2$ | Chlornitrofen |

Test Example 1

Cylindrical plastic pots (diameter, 10 cm; height, 10 cm) were filled with upland field soil, and the seeds of velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 10.

TABLE 10

| Compound No. | Dosage (g/are) | Herbicidal activity Velvetleaf |
|---|---|---|
| 1 | 1.25 | 5 |
| 2 | 1.25 | 5 |
| 3 | 1.25 | 5 |

TABLE 10-continued

| Compound No. | Dosage (g/are) | Herbicidal activity Velvetleaf |
|---|---|---|
| 4 | 1.25 | 5 |
| 5 | 1.25 | 5 |
| 6 | 1.25 | 5 |
| 7 | 1.25 | 5 |
| 8 | 1.25 | 5 |
| 9 | 1.25 | 5 |
| 10 | 1.25 | 5 |
| 11 | 1.25 | 5 |
| A | 1.25 | 0 |

Test Example 2

Cylindrical plastic pots (diameter, 10 cm; height, 10 cm) were filled with upland field soil, and the seeds of Japanese millet and tall morningglory were sowed therein and covered with soil. A designated amount of the test compound formulated in an emulsifiable concentrate as in Formulation Example 2 was diluted with water, and the dilution was sprayed onto the soil surface by means of a small hand sprayer at a sprayer volume of 10 liters per are. The test plants were grown in a greenhouse for 20 days, and the herbicidal activity was examined. The results are shown in Table 11.

TABLE 11

| Compound No. | Dosage (g/are) | Herbicidal activity | |
|---|---|---|---|
| | | Japanese millet | Tall morning-glory |
| 2 | 5 | 5 | 5 |
| 3 | 5 | 5 | 5 |
| 4 | 5 | 5 | 5 |
| 6 | 5 | 5 | 5 |
| 8 | 5 | 5 | 5 |
| 9 | 5 | 5 | 5 |
| 10 | 5 | 5 | 5 |

Test Example 3

Cylindrical plastic pots (diameter, 10 cm; height, 10 cm) were filled with upland field soil, and the seeds of tall morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 12.

TABLE 12

| Compound No. | Dosage (g/are) | Herbicidal activity | | |
|---|---|---|---|---|
| | | Tall morning-glory | Radish | Velvet-leaf |
| 1 | 1.25 | 5 | 4 | 5 |
| 2 | 1.25 | 5 | 5 | 5 |
| 3 | 1.25 | 5 | 5 | 5 |
| 4 | 1.25 | 5 | 5 | 5 |
| 5 | 1.25 | 5 | 4 | 5 |
| 6 | 1.25 | 5 | 4 | 5 |
| 7 | 1.25 | 5 | 4 | 5 |
| 8 | 1.25 | 5 | 5 | 5 |
| 9 | 1.25 | 5 | 5 | 5 |
| 10 | 1.25 | 5 | 5 | 5 |
| A | 1.25 | 0 | 0 | 0 |

Test Example 4

Cylindrical plastic pots (diameter, 10 cm; height, 10 cm) were filled with upland field soil, and the seeds of Japanese millet and oats were sowed and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 13.

TABLE 13

| Compound No. | Dosage (g/are) | Herbicidal activity | |
|---|---|---|---|
| | | Japanese millet | Oats |
| 2 | 1.25 | 4 | 5 |
| 3 | 1.25 | 5 | 5 |
| A | 1.25 | 0 | 0 |

Test Example 5

Cylindrical plastic pots (diameter, 8 cm; height, 12 cm) were filled with paddy field soil, and the seeds of barnyardgrass, broad-leaved weeds (common falsepimpernel, indian toothcup, waterwort) were sowed therein in a depth of 1 to 2 cm. After flooding, rice seedlings of 2-lead stage were transplanted and cultivated in a greenhouse. Six days thereafter (the early stage of weed germination), a designated amount of the test compound formulated in an emulsifiable concentrate as in Formulation Example 2 was diluted with water (5 ml), and applied onto water surface. The test plants were further frown in the greenhouse for 20 days, and the herbicidal activity and the phytotoxicity were examined. The results are shown in Table 14.

TABLE 14

| Compound No. | Dosage (g/are) | Phytotoxicity Rice plant | Herbicidal activity | |
|---|---|---|---|---|
| | | | Barnyard-grass | Broad-leaved weeds |
| 1 | 0.63 | 0 | 4 | 5 |
| 2 | 0.63 | 1 | 5 | 5 |
| 3 | 0.16 | 1 | 4 | 5 |
| 4 | 0.63 | 0 | 4 | 5 |
| 5 | 0.63 | 0 | 4 | 5 |
| 6 | 0.63 | 1 | 5 | 5 |
| 7 | 0.63 | 0 | 4 | 5 |
| A | 0.63 | 0 | 3 | 3 |

Test Example 6

Vats (33 cm×23 cm×11 cm) were filled with upland field soil, and the seeds of cotton, velvetleaf, black nightshade, johnsongrass and giant foxtail were sowed therein in a depth of 1 to 2 cm. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and the phytotoxicity were examined. The results are shown in Table 15.

TABLE 15

| Compound No. | Dosage (g/are) | Phytotoxicity Cotton | Herbicidal activity | | | |
|---|---|---|---|---|---|---|
| | | | Velvet-leaf | Black night-shade | Johnson-grass | Giant fox-tail |
| 2 | 2.5 | 0 | 5 | 5 | 4 | 5 |
| 3 | 2.5 | 1 | 5 | 5 | 5 | 5 |
| A | 2.5 | 0 | 0 | 0 | 0 | 0 |

Test example 7

Vats (33 cm × 23 cm × 11 cm) were filled with upland field soil, and the seeds of wheat, barley, pale smartweed, persian speedwell, field pansy, blackgrass, annual bluegrass and wild oats were sowed therein in a depth of 1 to 2 cm. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 27 days, and the herbicidal activity and the phytotoxicity were examined. The results are shown in Table 16.

TABLE 16

| Compound No. | Dosage (g/are) | Phytotoxicity | | Herbicidal activity | | | | | |
|---|---|---|---|---|---|---|---|---|---|
| | | Wheat | Barley | Pale smart-weed | Persian speed-well | Field pansy | Black grass | Annual blue-grass | wild oats |
| 2 | 1.25 | — | 1 | 4 | 5 | 5 | — | 4 | 4 |
| 3 | 1.25 | 1 | 1 | 5 | 5 | 5 | 5 | 5 | 4 |
| A | 1.25 | 0 | 0 | 0 | 0 | 0 | 0 | 0 | 0 |

Test Example 8

Vats (33 cm × 23 cm × 11 cm) were filled with upland field soil, and the seeds of soybean, corn, rice plane, velvetleaf, redroot pigweed and black nightshade, were sowed therein and cultivated in a greenhouse for 18 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in a greenhouse for 20 days, and the herbicidal activity and the phytotoxicity were examined. At the time of the application, the test plants were generally at the 1 to 4 leaf stage and in 2 to 20 cm height, although the growing stage of the test plants varied depending on their species. The results are shown in Table 17.

TABLE 17

| Compound No. | Dosage (g/are) | Phytotoxicity | | | Herbicidal activity | | |
|---|---|---|---|---|---|---|---|
| | | Soy-bean | Corn | Rice plant | Velvet-leaf | Redroot pigweed | Black night-shade |
| 2 | 0.16 | 1 | 0 | 1 | 5 | 4 | 4 |
| 3 | 0.16 | 1 | 1 | 1 | 4 | 5 | 5 |
| 4 | 0.63 | 1 | 1 | 1 | 4 | 4 | — |
| A | 0.63 | 0 | 0 | 0 | 2 | 2 | 2 |

What is claimed is:

1. A compound of the formula:

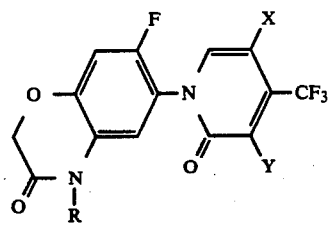

wherein R is a $C_1$–$C_8$ alkyl group, a $C_3$–$C_7$ alkenyl group, a $C_3$–$C_6$ alkynyl group, a $C_2$–$C_4$ haloalkyl group, a $C_3$–$C_4$ haloalkenyl group or a $C_1$–$C_4$ alkoxy-$C_1$–$C_2$ alkyl group, X is a hydrogen atom, a halogen atom, a methyl group optionally substituted with not more than 3 halogen atoms or an ethyl group optionally substituted with not more than 5 halogen atoms and Y is a hydrogen atom or a methyl group.

2. The compound according to claim 1, wherein R is a $C_2$–$C_4$ alkyl group, a $C_3$–$C_4$ alkenyl group, a $C_3$–$C_4$ alkynyl group, a 2-fluoroethyl group or a $C_1$–$C_3$ alkoxymethyl group, X is a hydrogen atom, a fluorine atom, a chlorine atom, a bromine atom, a methyl group, a fluoromethyl group or a difluoromethyl group and Y is a hydrogen atom or a methyl group.

3. The compound according to claim 1, wherein R is an n-propyl group, an isopropyl group, a sec-butyl group, a $C_3$–$C_4$ alkenyl group, a $C_3$–$C_4$ alkynyl group, a 2-fluoroethyl group or a methoxymethyl group, X is a fluorine atom, a chlorine atom, a bromine atom or a methyl group and Y is a hydrogen atom or a methyl group.

4. The compound according to claim 1, which is 1-(7-fluoro-4-propargyl-3-oxo-3,4-dihydro-2H-1,4-benzoxazin6-yl) -4-trifluoromethyl-2-pyridone.

5. The compound according to claim 1, which is 5-chloro-1-(7-fluoro-4-propargyl-3-oxo-3,4-dihydro-2H-1,4-benzoxazin-6-yl) -4-trifluoromethyl-2-pyridone.

6. The compound according to claim 1, which is 1-(7-fluoro-4-propargyl-3-oxo-3,4-dihydro-2H-1,4-benzoxazin-6-yl) -5-methyl-4-trifluoromethyl-2-pyridone.

7. A herbicidal composition which comprises as an active ingredient a herbicidally effect amount of the compound according to claim 1, and an inert carrier or diluent.

8. A method for exterminating harmful weeds, which comprises applying a herbicidally effective amount of the compound according to claim 1 and an inert carrier or diluent to the area where the undesired weeds grow or will grow.

* * * * *